(12) United States Patent
Wolfschoon-Pombo et al.

(10) Patent No.: US 7,579,029 B2
(45) Date of Patent: Aug. 25, 2009

(54) PROCESS FOR INCORPORATING WHEY PROTEINS INTO FOODSTUFFS

(75) Inventors: Alan F. Wolfschoon-Pombo, Freising (DE); Thomas L. Spiegel, Munich (DE)

(73) Assignee: Kraft Foods Global Brands LLC, Northfield, IL (US)

( * ) Notice: Subject to any disclaimer, the term of this patent is extended or adjusted under 35 U.S.C. 154(b) by 472 days.

(21) Appl. No.: 10/673,535

(22) Filed: Sep. 29, 2003

(65) Prior Publication Data

US 2004/0151803 A1 Aug. 5, 2004

Related U.S. Application Data

(63) Continuation of application No. PCT/US02/10887, filed on Apr. 8, 2002.

(30) Foreign Application Priority Data

Apr. 9, 2001 (EP) .................. 01107852

(51) Int. Cl.
*A23C 19/00* (2006.01)
(52) U.S. Cl. ............... 426/41; 426/34; 426/42; 426/580; 426/582
(58) Field of Classification Search ............ 426/34, 426/36, 38, 41, 42, 519, 580, 582, 583, 585, 426/586, 601, 613, 656
See application file for complete search history.

(56) References Cited

U.S. PATENT DOCUMENTS

| | | | |
|---|---|---|---|
| 3,922,375 A | 11/1975 | Ernesto et al. | |
| 3,930,039 A | 12/1975 | Kuipers | |
| 3,956,520 A | 5/1976 | Aiello | |
| 4,188,411 A | 2/1980 | Kuipers et al. | |
| 5,350,590 A | 9/1994 | McCarthy et al. | |

FOREIGN PATENT DOCUMENTS

| | | | |
|---|---|---|---|
| EP | 0398408 | | 11/1990 |
| EP | 0603981 | | 6/1994 |
| EP | 0787436 | | 8/1997 |
| EP | 0818149 | | 1/1998 |
| EP | 0 966 887 | | 12/1999 |
| GB | 1440182 | * | 6/1976 |
| WO | WO9836647 | | 8/1998 |

OTHER PUBLICATIONS

PCT International Search Report for Application No. PCT/IE98/0002 dated Jun. 8, 1998.

* cited by examiner

*Primary Examiner*—Leslie Wong
(74) *Attorney, Agent, or Firm*—Fitch, Even, Tabin & Flannery

(57) ABSTRACT

The present invention is concerned with the incorporation of whey proteins into foodstuffs by acidifying an aqueous solution of one or more whey proteins below their isoelectric pH, optionally forming a whey protein-stabilized fatty emulsion by blending and homogenizing said acidified solution of whey proteins with one or more fats, heat-treating said acidified solution or whey protein-stabilized fatty emulsion and blending same with a foodstuff base to form a foodstuff, and optionally blending and incubating the food stuff with transglutaminase.

8 Claims, No Drawings

PROCESS FOR INCORPORATING WHEY PROTEINS INTO FOODSTUFFS

This is a continuation of prior application Ser. No PCT/US02/10887, designating the U.S., filed Apr. 8, 2002, which claims the benefit of Europe application number 01107852.4, filed on Apr. 9, 2001. PCT/US02/10887 is hereby incorporated herein by reference in its entirety.

The present invention is concerned with the incorporation of whey proteins into foodstuffs. In particular, the invention relates to a process for preparing a whey protein-stabilized fatty emulsion, the thus obtainable whey protein-stabilized fatty emulsion, a process for incorporating whey proteins into a foodstuff using said emulsion or an acidified solution of whey proteins, and the foodstuff thus obtainable.

In the field of the manufacture of food, several attempts have been made to introduce larger amounts of whey proteins, for example to replace costly casein proteins and utilize wasted but rich whey proteins, without a resulting gumminess (texture effect). With respect to the example of process cheese, it has been practically impossible to incorporate larger amounts of whey proteins over a weight ratio of whey protein to casein of about 10:90. The higher the amount of whey proteins, the gummier and softer is the resultant cheese.

The following documents, the disclosure of which is incorporated herein by reference, represent technological background material on whey proteins, their properties and usage in foods:

Kinsella, J. E.; Whitehead, D. M. (1989): Proteins in whey: Chemical, physical, and structural properties. Advances in Food and Nutrition Research, 33, 343-438

Konrad, G.; Lieske, B. (1994): Gezielte thermische Denaturierung—ein alternativer Weg zu funktionellerem Molkenprotein. Deutsche Milchwirtschaft, 45, 1130-1134

Lupano, C. (1994): Effect of heat treatments in very acidic conditions on whey protein isolate properties. Journal of Dairy Science, 77, 2191-2198

Patocka, G.; Drathen, M.; Jelen, P. (1987): Heat stability of isolated whey protein fractions in highly acidic condtions. Milchwissenschaft, 42, 700-705

Shimizu, M.; Saito, M.; Yamauchi, K. (1985): Emulsifying and structrual properties of β-lactoglobulin at different pHs. Agricultural and Biological Chemistry, 49, 189-194

Strandholm, J. J.; Prochnow, R. R.; Miller, M. S.; Woodford, L. E.; Naunaber, S. M. (1989): Method for controlling melting properties of process cheese. U.S. Pat. No. 4,885,183

Swartz, M. L. (1988): Beverage cloud based on a whey protein-stabilized lipid. U.S. Pat. No. 4,790,998

Yamauchi, K.; Shimizu, M.; Kamiya, T. (1980): Emulsifying properties of whey protein. Journal of Food Science, 45, 1237-1242

As regards the structural and textural properties of foods, one possibility to increase the firmness thereof would be the polymerization of the proteins by an enzyme, namely a transglutaminase. However, transglutaminases predominantly polymerize caseins, whereas their reactivity towards whey proteins is very low or even absent. Thus, the effect of enzymatic treatment on whey protein-enriched food compositions is considerably low.

The following documents represent technological background material on transglutaminases, their effect on proteins and usage in foods:

Aboumahmoud, R.; Savello, P. (1990): Cross-linking of whey proteins by transglutaminase. Journal of Dairy Science 73, 256-263

Budolfsen, G.; Nielsen, P. M. (1999): Method for production of an acidified edible gel on milk basis. U.S. Pat. No. 5,866,180

Chanyongvorakul, Y.; Matsumara, Y.; Sawa, A.; Nio, N.; Mori, T. (1997): Polmyerization of β-lactoglobulin and bovine serum albumin at oil-water interfaces in emulsions by transglutaminase. Food Hydrocolloids 11, 449-455

Faergemand, M.; Murray; B. S.; Dickinson, E. (1997): Cross-linking of milk proteins at the oil-water interface. Journal of Agricultural and Food Chemistry 45, 2514-2519

Faergemand, M.; Otte, J.; Qvist, K. B. (1997): Enzymatic cross-linking of whey proteins by a $Ca^{2+}$-independent microbial transglutaminase from Streptomyces lydicus. Food Hydrocolloids 11, 19-25

Feargemand, M.; Otte, J.; Qvist, K. B. (1997): Emulsifying properties of milk proteins cross-linked with microbial transglutaminase. International Dairy Journal 8, 715-723

Kuraishi, T.; Sakamoto, J.; Soeda, T. (1996): Production of cheese using transglutaminase. Patent Application EP 0 711 504 (JP 81-73032 A2)

Soeda, T. (1999): Cheese whey protein having improved texture, process for producing the same and use thereof. Patent Application EP 0 966 887

Traoré, F.; Meunier, J. C. (1992): Cross-linking activity of placental FXIIIa on whey proteins and caseins. Journal of Agricultural and Food Chemistry 40, 399-402

Tsukasaki, F.; Minagawa, E.; Mikami, T.; Nonaka, M.; Motoki, M. (1990): Preparation of cheese food. Patent JP 21-31537 A2

Yamamoto, Y. (1996): Rheology of milk protein gels and protein-stabilized emulsions cross-linked by transglutaminase. Journal of Agricultural and Food Chemistry 44, 1371-1377

In view of the above, the present inventors thoroughly studied the properties of aqueous solutions of whey proteins and conceived new ways to modify such proteins, thus providing a solution to the problems of the prior art as outlined above.

Accordingly, in a first aspect, the present invention provides a process for preparing a whey protein-stabilized fatty emulsion, comprising the steps of acidifying an aqueous solution of one or more whey proteins below their isoelectric pH, blending and homogenizing the acidified solution of whey proteins with one or more fats to form a whey protein-stabilized fatty emulsion, and heat-treating said whey protein-stabilized fatty emulsion at a temperature of more than 80° C.

Potential sources for the whey proteins referred to herein are whey protein concentrates (WPC) and whey protein isolates (WPI), either as reconstituted WPC and/or WPI powders or preferably as liquid concentrates such as ultrafiltrated whey. Likewise, normal whey powder may represent a source for the whey proteins referred to in this description. The whey can be rennet whey or acid whey. Microfiltration permeate obtained by using, e.g., a 0.1 μm membrane, which permeate contains the native whey proteins, and the ultrafiltrated concentrate thereof may also be used. A combination of one or more whey protein sources may be utilized to provide whey proteins in the present invention.

The whey proteins initially used in the present invention may be native or denatured whey proteins, with preference given to predominantly native whey proteins. However, particulate and highly denatured whey proteins also exhibit very good effects in the present invention.

The protein content in the aqueous solution of one or more whey proteins is preferably at least 4% by weight (with total solids being, for example, about 10% or more) to reach the desired whey protein content in the final food products.

The maximum whey protein content is preferably about 20% by weight. More preferably, the whey protein content of the aqueous solution is in the range of 8 to 12% by weight (preferably 12 to 20% total solids).

In the first step of the process for preparing a whey protein-stabilized fatty emulsion, the aqueous solution of one or more whey proteins as outlined above is acidified below the isoelectric pH of the whey proteins contained in said solution. For the purpose of acidifying the whey protein solution, any acid may be used that is not objectionable to the intended application and use of the final whey protein-stabilized fatty emulsion. Specifically, any food grade acid such as lactic, citric, phosphoric or hydrochloric acid and any acidulant such as glucono-δ-lactone or vinegar may be used, alone or in combination of two or more thereof. The preferred acid is 90% lactic acid. Optionally, it is possible to employ a lactic acid producing bacterial culture in the presence of a suitable sugar such as glucose or lactose, optionally in combination with one or more of the acids mentioned before. In general, the concentration of the acid(s) and the temperature used during acidification are adjusted such that no detrimental effects are induced. For example, if there are caseins present in the solution, it may be necessary to adjust the initial concentration of the acid(s) and the temperature during acidification in such a way that no coagulation (flocculation) of caseins is induced. Similarly, too high (e.g. >65° C.) temperatures may induce a whey protein coagulation if the whey proteins are in the native state or not fully denatured. Accordingly, room (ambient) temperature represents a preferred temperature for a practical application.

The pH accomplished in the acidification step is preferably considerably below the isoelectric point of the whey proteins comprised in the aqueous solution. Thus, the pH reached is preferably in the range of 4.5 to 2.5, more preferably 4.0 to 3.5. As a reference, the isoelectric points of major whey proteins are: ~5.1 (β-lactoglobulin); 4.2-4.5 (α-lactalbumin); 4.7-4.9 (bovine serum albumin) and 6.3-7.0 (immunoglobulin G1).

In the acidification step, the aqueous solution of the whey proteins is preferably agitated when adding the acid in order to avoid local peak concentrations of the acid. Although it is also possible to add the aqueous solution of whey proteins to an aqueous solution of the acid(s), this may not be the preferred way of acidification due to potential detrimental peak acid concentrations. Preferably, the whey protein solution after addition of the acid is allowed to stand or is agitated until an equilibrium state is reached, for example, for one or more minutes, preferable about 10 to 30 minutes.

In the second step of the process for preparing a whey protein-stabilized fatty emulsion, the acidified solution of whey proteins is blended and homogenized with one or more fats. In this step, any fat may be used which is not objectionable to the desired application of the resulting fatty emulsion. The preferred fat is milk fat, e.g. in the form of cream, plastic cream and more preferably butter or anhydrous butter fat. However, other sources for fats may be used, especially vegetable fats and oils, or animal fat, such as beef tallow, depending on the application of the whey protein-stabilized fatty emulsion. A combination of two or more fats may be used. The one or more fats are used in an amount such that the ratio of whey protein to fat in the resulting fatty emulsion is in the range of preferably 3:1 to 1:5 (the total fat content in the fatty emulsion being preferably in the range of 3 to 30% by weight), more preferably 2:1 to 1:2.

The blending of the acidified solution of whey proteins with one or more fats is followed by a homogenization, i.e. a shear treatment. Blending and homogenizing the two components, i.e. acidified whey protein solution and fats, may be a combination of one or more steps. For example, the components may first be blended and subsequently subjected to a shear treatment, or blending may be effected simultaneously in the homogenization, for example by introducing the components into a homogenizer and starting the device. Preferably, blending and homogenizing is carried out in a single apparatus for economic reasons and effectiveness. The blending and homogenizing step may be carried out using a conventional homogenizer and is preferably carried out at a temperature of from 50 to 70° C. and a pressure of from 100 to 300 bar, depending on the fat content (lower pressures may be more suitable at higher fat levels). In general, the homogenization can be conducted at a temperature and pressure and for a period which are conventional in this art.

It is assumed that the resulting whey protein-stabilized fatty emulsion is of the oil-in-water emulsion type. However, this assumption should not be construed as restricting the scope of the present invention, and other structures such as water-in-oil or bicontinuous structures may be contemplated, depending on the components and amounts used thereof.

The blending and homogenizing step is followed by a heat treatment at a temperature of 80° C. or more, and optionally at an elevated pressure. The preferred temperature range for the heat treatment is 80 to 95° C., and the preferred holding time is in the range of 1 to 10 minutes, for example a heat treatment condition of a temperature of 85° C. and a holding time of 5 minutes. It is assumed that the subsequent heat treatment should modify the topography of the already changed whey proteins (due to the acidification below their isoelectric pH) to make them even more functional, for example in replacing casein in casein-containing foodstuffs.

Following the blending/homogenization or the heat treatment, the whey protein-stabilized fatty emulsion may be cooled (e.g., to room temperature) or directly used in the hot state in the desired application such as outlined below.

The whey protein-stabilized fatty emulsion obtainable by the process of the present invention preferably has a fat content in the range of from 3 to 30% by weight and a whey protein content in the range of from 5 to 15% by weight. In a preferred embodiment, an emulsion made in accordance with the process of the invention (e.g., by mixing WPC and butter) has 20 to 25% total solids, 5 to 10% fat, 8 to 12% protein and 3 to 5% sugars, based on the total weight of the emulsion (the presence of additional components such as sugars may result from the whey protein source such as WPC or the deliberate addition of further components).

The whey protein-stabilized fatty emulsion obtainable by the above process represents another aspect of the present invention.

The protein-stabilized fatty emulsion of the invention may be used for incorporating whey proteins into a foodstuff. Thus, in another aspect the present invention provides a process for incorporating whey protein into a foodstuff comprising the steps of blending the whey protein-stabilized fatty emulsion obtainable by the above process of the invention with a foodstuff base to form a foodstuff. In an alternative embodiment, the process for incorporating whey proteins into a foodstuff comprises the steps of acidifying an aqueous solution of one or more whey proteins below their isoelectric pH, heat-treating the acidified solution at a temperature of more than 80° C. and blending the acidified and heat-treated solution with a foodstuff base to form a foodstuff. In this alternative embodiment, the aspects, conditions and properties of acidifying an aqueous solution of one or more whey proteins below their isoelectric pH and heat-treating the acidified solution are as defined above having regard to the process for preparing a whey protein-stabilized fatty emulsion.

The foodstuff base may be any dairy or non-dairy based foodstuff base. In fact, the present inventors have found that using a specifically acidified and heat-treated whey protein solution or whey protein fatty emulsion provides a means for using higher amounts of whey proteins, or to incorporate more whey proteins, into other food systems. Preferably, the foodstuff base is a dairy based foodstuff base and more preferably a casein-containing foodstuff base. Moreover, the foodstuff base can be foodstuff base containing meat proteins. Specific examples of the foodstuff base are bases for cream cheese, process cheese, natural cheese and mayonnaise, as well as process meat products.

The conditions for blending the fatty emulsion and/or the acidified and heat-treated whey protein solution and the foodstuff base are those normally found in the manufacture (blending of raw materials) of foodstuffs, for example process cheese, cream cheese or natural cheese, or process meat. If the whey protein-stabilized fatty emulsion of the invention is used, the weight ratio of fatty emulsion to foodstuff base is preferably in the range of from 20:80 to 70:30. Similarly, if the acidified and heat-treated solution of one or more whey proteins is used, the weight ratio of whey proteins to foodstuff base is preferably in the range of from 20:80 to 70:30. If a casein-containing foodstuff base is used, the blending ratio of fatty emulsion or acidified whey protein solution to casein-containing foodstuff base is preferably such that the weight ratio of whey proteins to casein in the resulting casein-containing foodstuff is in the range of >10:90 to 80:20, more preferably 20:80 to 40:60. If a meat protein-containing foodstuff base is used, the blending ratio of fatty emulsion or acidified whey protein solution to meat protein-containing foodstuff base is preferably such that the weight ratio of whey proteins to meat proteins in the resulting meat protein-containing foodstuff is in the range of from 10:90 to 80:20, more preferably 20:80 to 40:60. Especially, if meat proteins are used, the resulting meat protein-containing foodstuff can also include animal fat, such as beef tallow.

If desired, the resulting foodstuff may be further blended and incubated with a transglutaminase enzyme. Normally, whey proteins do not react with transglutaminases. The present inventors have found that the pre-treatment of whey protein solutions in the acid pH range (below the isoelectric pH of the whey proteins) as described in this invention offers a possibility to modify the behavior of whey proteins also towards the action of transglutaminase. Accordingly, in another aspect of the present invention, the process for incorporating whey proteins into a foodstuff comprises the further step of blending and incubating the resulting foodstuff with the enzyme transglutaminase. As is generally known by the person skilled in the art, there are different transglutaminases, classified under the general nomenclature EC 2.3.2.13, and any of these transglutaminases can be used in the present invention. In particular, it is possible to use a transglutaminase produced by *Streptoverticilium mobaraense* which is commercially available under the name of "Aktiva-MP" from Ajinomoto. The enzyme employed is preferably used in conventional amounts such as 1 to 6 u/g (units enzyme per gram protein in the system). The incubating conditions are preferably a temperature in the range of 20 to 60° C., more preferably 50° C.; a duration of 5 to 60 minutes; and a pH of 5.5 to 7.5, more preferably 6 to 7. Preferably, no shear is applied during the incubation period.

The foodstuff which is obtainable by the process according to the invention, for example process cheese, cream cheese, natural cheese, mayonnaise or process meat, is superior as compared to foodstuffs of the prior art in that a high firmness and short texture of the resultant products can be accomplished even at high whey protein contents, which is not observed when native whey proteins are utilized. Specifically, if a casein-containing foodstuff is manufactured, such as a process cheese formulation, high protein to casein ratios of up to 80:20 by weight can be established together with a favorable appearance and excellent sensory properties.

EXAMPLE 1

A whey protein concentrate (17.7% total solids, 10% protein) with the majority of its proteins in their native state is acidified with lactic acid down to pH 3.8. Afterwards the acidified whey protein solution is blended with 5% molten butter at room temperature and homogenized at 220 bar and 60° C. The emulsion is then heat treated at 85° C. for 5 min. Then 34.2 parts of the heated emulsion are immediately blended with 3.5 parts of rennet casein, 3.5 parts of milk concentrate, 1.4 parts of starch, 7 parts of hard cheese, 15.9 parts of butter, 5.3 parts of whey powder, 3.0 parts of emulsifying salts, 1 part of salt and 25.2 parts of water so as to complete 100 parts. After thoroughly mixing, the blend is treated as in the conventional manufacture of process cheese spreads.

EXAMPLE 2

A whey protein concentrate (17.7% total solids, 10% protein) with the majority of its proteins in their native state is acidified with lactic acid down to pH 3.8. Afterwards the acidified whey protein solution is blended with 5% molten butter at room temperature and homogenized at 220 bar and 60° C. The emulsion is then heat treated at 85° C. for 5 min. Then 34.2 parts of the heated emulsion are immediately blended with 3.5 parts of rennet casein, 3.5 parts of milk concentrate, 1.4 parts of starch, 7 parts of hard cheese, 15.9 parts of butter, 5.3 parts of whey powder, 3.0 parts of emulsifying salts, 1 part of salt and 25.2 parts of water so as to complete 100 parts. After thoroughly mixing, the blend is incubated with a microbial transglutaminase (5 units per gram protein in the blend) at 50° C. for 1 h. The blend is then treated as in the conventional manufacture for process cheese spreads. The following table shows the firmness (Stevens Texture Analyzer) of the final cheese produced as described above compared to a standard product and a product with a native whey protein concentrate.

| Product | Whey protein: casein ratio | Transglutaminase | Firmness [g] |
| --- | --- | --- | --- |
| Standard | 10:90 | no | 57 |
|  |  | yes | 160 |
| With native whey protein | 45:55 | no | 36 |
|  |  | yes | 64 |
| With whey protein emulsion pH 3.8, heated | 45:55 | no | 42 |
|  |  | yes | 115 |

The invention claimed is:

1. A process for incorporating whey proteins into a foodstuff comprising:

blending a whey protein-stabilized fatty emulsion with a foodstuff base that includes casein to form a foodstuff, wherein the weight ratio of whey protein to casein is 10:90 to 80:20, wherein the whey protein-stabilized fatty emulsion is prepared by a process comprising acidifying an aqueous solution of one or more whey proteins below their isoelectric pH to a pH in the range of 4.5 to 2.5;

blending and homogenizing the acidified solution of whey proteins with one or more fats to form a whey protein-stabilized fatty emulsion, wherein the whey protein-stabilized emulsion has a fat content in the range of from 3 to 30 percent by weight and a whey protein content in the range of from 5 to 15 percent by weight; and heat-treating said whey protein-stabilized fatty emulsion at a temperature of more than 80° C., wherein the foodstuff is further blended and incubated with a transglutaminase.

2. The process of claim 1 wherein the weight ratio of whey protein to casein in the resulting casein-containing foodstuff is 20:80 to 40:60.

3. The process of claim 1 wherein the foodstuff base is a process cheese formulation.

4. The process of claim 1 wherein the foodstuff base contains meat proteins.

5. The process of claim 4 wherein the weight ratio of whey proteins to meat proteins in the resulting meat protein-containing foodstuff is in the range of from 10:90 to 80:20.

6. The process of claim 5 wherein the weight ratio of whey proteins to meat protein in the resulting meat protein-containing foodstuff is 20:80 to 40:60.

7. The process of claim 3 wherein the resulting meat protein-containing foodstuff includes animal fat.

8. The process of claim 3 wherein the foodstuff base is process meat base.

* * * * *

UNITED STATES PATENT AND TRADEMARK OFFICE
CERTIFICATE OF CORRECTION

PATENT NO. : 7,579,029 B2
APPLICATION NO. : 10/673535
DATED : August 25, 2009
INVENTOR(S) : Wolfschoon-Pombo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 989 days.

Signed and Sealed this

Fourteenth Day of September, 2010

David J. Kappos
*Director of the United States Patent and Trademark Office*